United States Patent [19]

Chan et al.

[11] Patent Number: 5,543,521
[45] Date of Patent: Aug. 6, 1996

[54] COMPOUNDS THAT MODULATE ENDOTHELIN ACTIVITY

[75] Inventors: Ming F. Chan, San Diego; Vitukudi N. Balaji, Encinitas, both of Calif.

[73] Assignee: Immunopharmaceutics, Inc., San Diego, Calif.

[21] Appl. No.: 180,575

[22] Filed: Jan. 12, 1994

Related U.S. Application Data

[63] Continuation of Ser. No. 886,387, May 19, 1992, abandoned.

[51] Int. Cl.$^6$ .............. C07D 487/04; C07D 207/16; A61K 31/495
[52] U.S. Cl. .............. 544/349; 544/244; 546/200; 546/201; 548/532; 548/533
[58] Field of Search .............. 544/349; 514/249

[56] References Cited

U.S. PATENT DOCUMENTS

| | | | |
|---|---|---|---|
| 3,920,660 | 11/1975 | Fontanella | 544/349 |
| 4,997,836 | 5/1991 | Sugihara et al. | 514/253 |
| 5,082,838 | 1/1992 | Naka | 514/211 |
| 5,114,918 | 5/1992 | Ishikawa | 514/11 |
| 5,187,195 | 2/1993 | Oohata | 514/686 |
| 5,198,548 | 3/1993 | Beylin | 546/136 |
| 5,230,999 | 7/1993 | Suzuki | 435/71 |
| 5,231,166 | 7/1993 | Masaki et al. | 530/324 |
| 5,240,910 | 8/1993 | Lam | 514/11 |
| 5,248,807 | 9/1993 | Fujimoto | 560/11 |
| 5,334,598 | 8/1984 | Bagley | 514/303 |

FOREIGN PATENT DOCUMENTS

| | | |
|---|---|---|
| 2067288 | 10/1992 | Canada. |
| 0411150 | 8/1990 | European Pat. Off.. |
| 0404525A2 | 12/1990 | European Pat. Off.. |
| 0405421A2 | 1/1991 | European Pat. Off.. |
| 0436189A1 | 7/1991 | European Pat. Off.. |
| 0457195A2 | 11/1991 | European Pat. Off.. |
| 0460679A2 | 12/1991 | European Pat. Off.. |
| 2354056 | 5/1974 | Germany. |
| 2259450 | 3/1993 | United Kingdom. |
| 938799 | 5/1993 | WIPO. |

OTHER PUBLICATIONS

Clozel I, Nature 365, 759 (Oct. 1993).
Clozel II, J. Cardiovasc. Pharmacology 22(Suppl 8) 5377 (1993).
Mihara, Eur. J. Pharmacology—Molec. Pharmacology Section 246, 33–38 (1993).
"Third Int. Conf. on Endothelin" Feb. 15–17, 1993, Abstracts, pp. 98, 19, 15, 37.
Benigni, Kidney Int. 44, 440 (1993).
Nirei, Life Sci 52, 1869–1874 (1993).
Chemical Abstracts vol. 106 1987, Abst. 33114a, Simazaki et al. Jpn. Kokai Tokkyo Koho JP 61,112,060, Piperazine derivatives.
Doherty, "Endothelin: A new challenge," *J. Medicinal Chem.*, 35(9):1493–1508 (1992).

Bolger et al., "Characterization of binding of the $Ca^{++}$ channel antagonist [$^3$H] nitrendipine, to guinea-pig ileal smooth muscle," *J. of Pharmacology and Experimental Therapeutics*, 225:291–309 (1983).
Williams et al., "Sarafotoxin S6c: An agonist which distinguishes between endothelin receptor subtypes," *Biochem. and Biophys. Research Commun.*, 175(2):556–561 (1991).
Ihara et al., "An endothelin receptor ($ET_A$) antagonist isolated from *Streptomyces Misakiensis*," *Biochem. and Biophys. Research Commun.*, 178(1):132–137 (1991).
Spinella et al., "Design and synthesis of a specific endothelin 1 antagonist: Effects on pulmonary vasoconstriction," *Proc. Natl. Acad. Sci. USA*, 88p:7443–7446 (1991).
Saeki et al., "[$Ala^{1,3,11,15}$] endothelin–1 analogs with $ET_B$ agonistic activity," *Biochem. and Biophys. Research Commun.*, 179(1):286–292 (1991).
Gu et al., "The inhibitory effect of [$D-Arg^1$, D–Phe, D–Try$^{7,}$ 9, Leu$^{11}$] substance P on endothelin–1 binding sites in rat cardiac membranes," *Biochem. and Biophys. Research Commun.*, 179(1):130–133 (1991).
Panek et al., "Endothelin and structurally related analogs distinguish between endothelin receptor subtypes," *Biochem. and Biophys. Research Commun.*, 183(2):566–571 (1992).

(List continued on next page.)

Primary Examiner—Mark L. Berch
Attorney, Agent, or Firm—Stephanie L. Seidman; Brown, Martin, Haller & McClain

[57] ABSTRACT

Compounds of formula (I) and pharmaceutical compositions containing the compounds of formula (I):

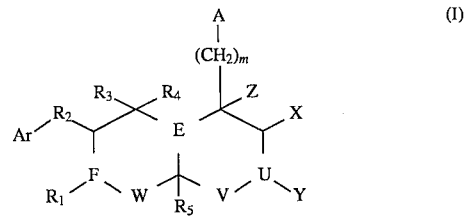

are provided. In formula (I): Ar is a substituted or unsubstituted aromatic or heterocyclic group; R is H or a substituted or unsubstituted straight or branched chain, cyclic or mixture of straight branched and cyclic alkyl, alkenyl, or alkynyl group having from 1–20 carbon atom; A is a functional group that bears a polar moiety; $R_1$ is R, R—C=0, R substituted with one or more heteroatoms, a substituted or unsubstituted aryl group, or is aryl-$(CH_2)_n$; $R_2$ is $(CH_2)_n$, CHR, $C(R)_2$, COO, OCO, NHCO, CONH, SO, $SO_2$ or NR; $R_3$ and $R_4$, which are the same or different or each may be absent, and are =O, H, O-aryl, OR, O-alkyl or alkyl, aryl, SR, S-aryl, NHR, NH-aryl, NR, or are other heteroaromatic groups; $R_5$ is H, OH or R; E and F, which are the same or are different, are either N or $(CH_2)_p$; p is an integer or 0 between 0 and 5; m and n are integers or 0 between 0 and 10; T is O, S, NCOR or NR; U and V, which may be the same or different, are $(CH_2)n$; W is CO, $(CH_2)n$, $(CH_2)_n$—CHR or CHR—$(CH_2)_n$; X and Y, which may be the same or different, are H, alkyl or aryl or X and Y form a saturated or unsaturated homocyclic or heterocyclic ring contain 3–15 members; and Z is H, SR, NHR or $N(R)_2$.

6 Claims, 1 Drawing Sheet

OTHER PUBLICATIONS

Ihara et al., "Biological profiles of highly potent novel endothelin antagonists selective for the $ET_A$ receptor," *Life Sciences*, 50:247–255 (1991).

Hirata et al., "Receptor binding activity and cytosolic free calcium response by synthetic endothelin analogs in culture rat vascular smooth muscle cells," *Biochem. and Biophys. Research Commun.*, 160:228–234 (1989).

Nakajima et al., "Synthesis of endothelin–1 analogues, endothelin–3, and sarafotoxin S6b: Structure–activity relationships," *J. of Cardiovascular Pharm.*, 13(Suppl. 5):S8–S12 (1989).

Yanagisawa et al., "A novel potent vasoconstrictor peptide produced by vascular endothelial cells," *Nature*, 332:411–415 (1988).

Kashiwabara et al., "Putative precursors of endothelin have less vasoconstrictor activity in vitro but a potent pressor effect in vivo," *FEBS Letters*, 247(1):73–76 (1989).

von Geldern et al., "A fluorogenic assay for endothelin–converting enzyme," *Peptide Research*, 4(1):32–35 (1991).

Inoue et al., "The human endothelin family: Three structurally and pharmacologically distinct isopeptides predicted by three separate genes," *Proc. Natl. Acad. Sci. USA*, 86:2863–2867 (1989).

Saida et al., "A novel peptide, vasoactive intestinal contractor, of a new (endothelin) peptide family," *J. Biol. Chem.*, 264(25):14613–14616 (1989).

Brooks et al., "Effect of nifedipine on cyclosporine A–induced nephrotoxicity, urinary endothelin excretion and renal endothelin receptor number," *Eur. J. of Pharmacology*, 194:115–117 (1991).

Bolger et al., "Vascular reactivity, tissue levels, and binding sites for endothelin: A comparison in the spontaneously hypertensive and Wistar–Kyoto rats," *Can. J. Physiol. Pharm.*, 69:406–413 (1990).

Simonson et al., "Endothelin–1 stimulates contraction of rat glomerular mesangial cells and potentiates β–Adrenergic–mediated cyclic adenosine monophosphate accumulation," *J. Clin. Invest.*, 85:790–797 (1990).

Stewart et al., "Increased plasma endothelin–1 in pulmonary hypertension: Marker or mediator of disease?" *Annals of Internal Medicine*, 114(6):464–469 (1991).

Takayanagi et al., "Presence of non–selective type of endothelin receptor on vascular endothelium and its linkage to vasodilation," *FEBS Letters*, 282(1):103–106 (1991).

Nishikori et al., "Receptor binding affinity and biological activity of C–terminal elongated forms of endothelin–1," *Neurochem. Int.*, 18(4):535–539 (1991).

Castiglione et al., "Alanine scan of endothelin," Peptides: Chemistry and Biology, Proc. Amer. Rept. Symp. (Twelfth), J. A. Smith and J. E. Rivier, Eds., ESCOM, Leiden, 1992, pp. 402–403.

Galantino et al., "D–Amino acid scan of endothelin," Peptides: Chemistry & Biology, Proc. Amer. Report. Symp. (Twelfth), J. A. Smith and J. E. Rivier, Eds., ESCOM, Leiden, 1992, pp. 404–405.

Filep et al., "Endothelin–1 induces prostacyclin release from bovine aortic endothelial cells," *Biochem. and Biophys. Research Comm.*, 177(1):171–176 (1991).

Spokes et al., "Studies with endothelin–3 and endothelin–1 on rat blood pressure and isolated tissues: Evidence for multiple endothelin receptor subtypes," *J. of Cardiovascular Pharmacology*, 13(Suppl. 5):S191–S192 (1989).

Cardell et al., "Two functional endothelin receptors in guinea–pig pulmonary arteries," *Neurochem. Int.*, 18(4):571–574 (1991).

Borges et al., "Tissue selectivity of endothelin," *Eur. J. of Pharmacology*, 165:223–230 (1989).

Ogawa et al., "Molecular cloning of a non–isopeptide–selective human endothelin receptor," *Biochem. and Biophys. Research Comm.*, 178(1):248–255 (1991).

Schvartz et al., "Bovine cerebellum endothelin receptor: Solubilization and identification," *Endocrinology*, 126(6):23218–3222 (1990).

Saudek et al, "Solution conformation of endothelin–1 by $^1$H NMR, CD, and molecular modeling," *Int. J. Peptide Protein Res.*, 37:174–179 (1991).

Aumelas et al., "Determination of the structure of [Nle$^7$]–endothelin by $^1$H NMR," *Int. J. Peptide Protein Res.*, 37:315–324 (1991).

Perkins et al., "Proposed solution structure of endothelin," *Int. J. Peptide Protein Res.*, 36:128–133 (1990).

Spinella et al., "A proposed structural model of endothelin," *Peptide Research*, 2(4):286–291 (1989).

Saudek et al., "$^1$H–NMR study of endothelin, sequence–specific assignment of the spectrum and a solution structure," *FEBS Letters*, 257(1):145–148 (1989).

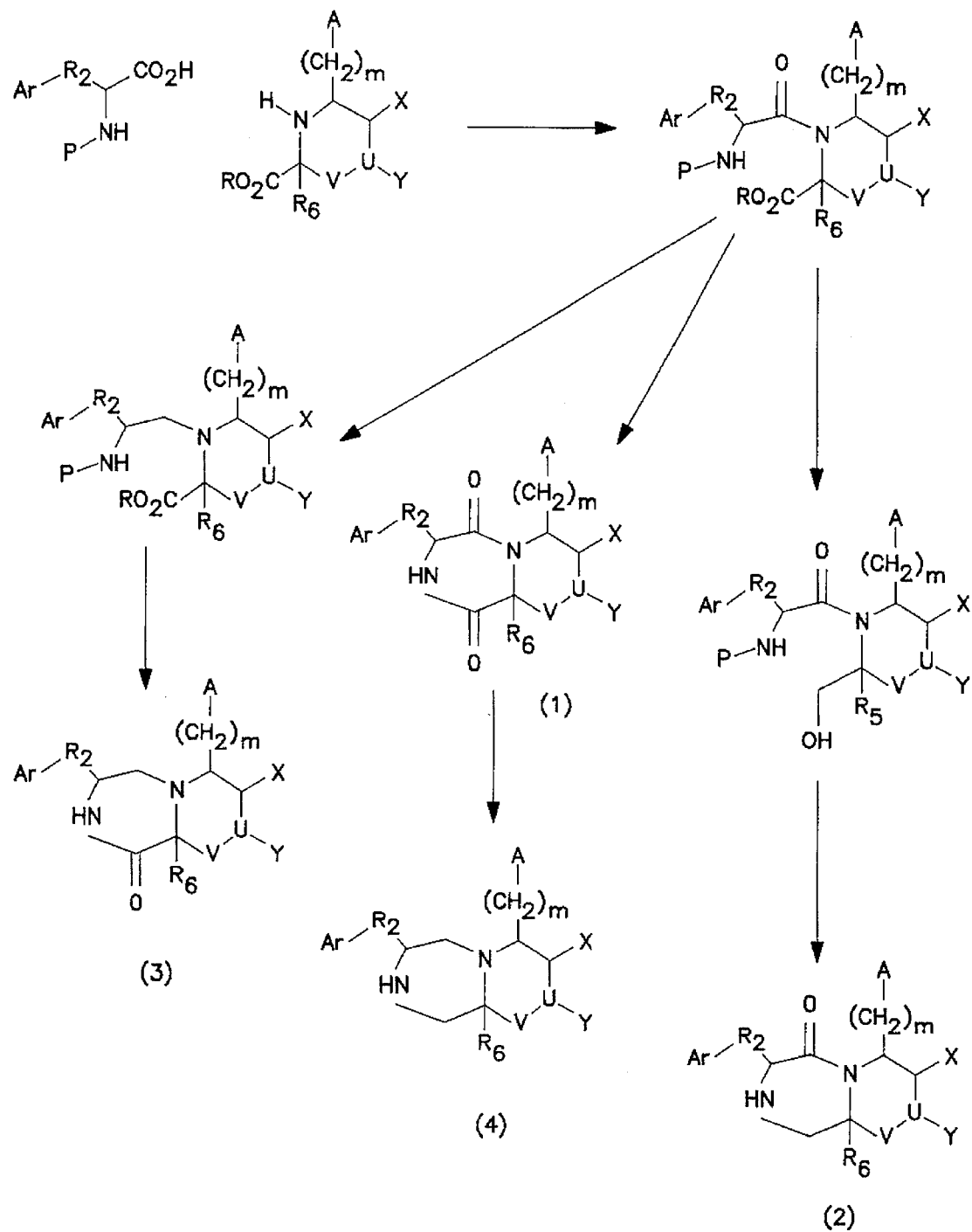

COMPOUNDS THAT MODULATE ENDOTHELIN ACTIVITY

This is a continuation of application Ser. No. 07/886,387, filed May 19, 1992, now abandoned.

FIELD OF THE INVENTION

The present invention relates to compounds that modulate or alter the activity of the endothelin family of peptides. More particularly, compounds that inhibit the activity of endothelin and that thereby possess therapeutic utility are provided.

BACKGROUND OF THE INVENTION

The vascular endothelium releases a variety of vasoactive substances, including the endothelium-derived vasoconstrictor peptide, endothelin (ET) (see, e.g., Vanhoutte et al. (1986) *Annual Rev. Physiol.* 48: 307–320; Furchgott and Zawadski (1980) *Nature* 288: 373–376). Endothelin-1, which is a potent twenty-one amino acid peptide vasoconstrictor that was originally identified in the culture supernatant of porcine aortic endothelial cells (see, Yanagisawa et al. (1988) *Nature* 332: 411–415), is the most potent vasopressor known. It is produced by numerous cell types, including the cells of the endothelium, trachea, kidney and brain. Endothelin is synthesized as a precursor of 203 amino acids, called preproendothelin, containing a signal sequence which is cleaved by an endogenous protease to produce a 38 (human) or 39 (porcine) amino acid peptide. This intermediate, referred to as big endothelin, is processed to the mature biologically active form in vivo by a putative endothelin-converting enzyme (see, e.g., Kashiwabara et al. (1989) *FEBS Lttrs.* 247: 337–340). Cleavage is required for induction of physiological responses (see, e.g., von Geldern et al. (1991) *Peptide Res.* 4: 32–35. The endothelin converting enzyme (ECE) appears to be a metal-dependent neutral protease. In porcine aortic endothelial cells, the 39 amino acid intermediate, big endothelin, is hydrolyzed at the $Trp^{21}$—$Val^{22}$ bond to generate endothelin-1 and a C-terminal fragment. A similar cleavage occurs in human cells from a 38 amino acid intermediate.

Three distinct endothelin isopeptides, endothelinol, endothelin-2 and endothelin-3, that exhibit potent vasoconstrictor activity have been identified. Each induces vasoconstriction with a potency order of endothelin-2>endothelinol>endothelin-3. In addition, the sarafotoxins (SRTX) S6, a group of peptide toxins from the venom of the snake *Atractaspis eingadensis* have structural and functional homology to endothelin-1 and bind competitively to the same cardiac membrane receptors. Sarafotoxins cause severe coronary vasospasm in snake bite victims (Kloog et al. (1989) *Trends Pharmacol. Sci.* 10: 212–214).

The family of three isopeptides endothelin-1, endothelin-2 and endothelin-3 are encoded by a family of three genes (see, Inoue et al. (1989) *Proc. Natl. Acad. Sci. USA* 86: 2863–2867; see, also Saida et al. (1989) *J. Biol. Chem.* 264: 14613–14616). The nucleotide sequences of the three human genes are highly conserved within the region encoding the mature 21 amino acid peptides. Endothelin-2 is ($Trp^6$,$Leu^7$) endothelin-1 and endothelino-3 is ($Thr^2$, $Phe^4$, $Thr^5$, $Tyr^6$, $Lys^7$, $Tyr^{14}$) endothelin-1. These peptides are, thus, highly conserved at the C-terminal ends. In addition, endothelin is highly conserved among species.

Release of endothelins from cultured endothelial cells is modulated by a variety of chemical and physical stimuli and appears to be regulated at the level of transcription and/or translation. For example, gene expression of endothelin-1 is increased by adrenaline, thrombin and $Ca^{2+}$ ionophore. The production and release of endothelin from the endothelium is stimulated by angiotensin II, vasopressin and other factors, such as endotoxin and cyclosporin (see, Brooks et al. (1991) *Eur. J. Pharm.* 194: 115–117), and is inhibited by nitric oxide. Endothelial cells appear to secrete short-lived endothelium-derived relaxing factors (EDRF), such as nitric oxide or a related substance (Palmer et al. (1987) *Nature* 327: 524–526), when stimulated by vasoactive agents, such as acetylcholine and bradykinin. Endothelin-induced vasoconstriction is also attenuated by atrial natriuretic peptide (ANP).

In vivo and in vitro, the endothelin peptides exhibit numerous biological activities. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produces long-lasting pressor effects and contraction, respectively (see, e.g., Bolger et al. (1991) *Can. J. Physiol. Pharmacol.* 69: 406–413). For example, in isolated vascular strips, endothelin-1 is a potent ($EC_{50}$=$4\times10^{-10}$M) and slow acting, but persistent, contractile agent. In vivo, a single dose elevates blood pressure in about 20 to 30 minutes. In addition to vasoconstriction, endothelin mediates renin release, stimulation of ANP release and induces a positive inotropic action in guinea pig atria. In the lung, endothelin-1 acts as a potent bronchoconstrictor (Maggi et al. (1989) *Eur. J. Pharmacol.* 160: 179–182). Endothelin increases renal vascular resistance, decreases renal blood flow, and decreases glomerular filtrate rate. It is a potent mitogen of glomerular mesangial cells and invokes the phosphoinoside cascade in such cells (Simonson et al. (1990) *J. Clin. Invest.* 85: 790–797).

Endothelin-1 plasma levels in healthy individuals, as measured by radioimmunoassay (RIA), are about 0.26–5 pg/ml. Blood levels of endothelin-1 and its precursor, big endothelin, are elevated in shock, myocardial infarction, vasospastic angina, kidney failure and a variety of connective tissue disorders. Increased levels of circulating endothelin are present in patients with pulmonary hypertension. In patients undergoing hemodialysis or kidney transplantation or suffering from cardiogenic shock, myocardial infarction or pulmonary hypertension levels are as high as 35 pg/ml have been observed (see, Stewart et al. (1991) *Annals Internal Med.* 114: 464–469). The levels of endothelin at the endothelium/smooth muscle interface are probably much higher because endothelin-1 likely acts as a local, rather than a systemic, regulating factor. Because of these numerous physiological effects, endothelin is believed to play a critical role in some pathophysiological conditions, such as hypertension, renal failure, asthma, endotoxin shock and vasospasm (see, Saito et al. (1990) *Hypertension* 15: 734–738; Tomita et al. (1989) *N.Engl.J. Med.* 321: 1127; Kurihara et al, (1989) *J. Cardiovasc. Pharmacol.* 13(*Suppl.* 5): S13–S17); Morel et al. (1989) *Eur. J. Pharmacol.* 167: 427–428).

Endothelin-induced vasoconstriction is not affected by antagonists to known neurotransmitters or hormonal factors, but is abolished by calcium channel antagonists. The effect of calcium channel antagonists, however, is most likely the result of blockage of calcium influx, since calcium influx appears to be required for the long-lasting contractile response to endothelin.

There are specific high affinity binding sites ($K_d$'s in the range of $2-6\times10^{-10}$M) for the endothelins in the vascular system and in other tissues, including the intestine, heart, lungs, kidneys, spleen, adrenal glands and brain. Binding is not inhibited by catecholamines, vasoactive peptides, neurotoxins or calcium channel antagonists. Endothelin binds and interacts with receptor sites that are distinct from other autonomic receptors and voltage dependent calcium channels. Competitive binding studies indicate that there are multiple classes of receptors with different affinities for the endothelin isopeptides.

DNA clones encoding two distinct endothelin receptors, designated $ET_A$ and $ET_B$, have been isolated (Arai et al. (1990) *Nature* 348: 730–732; Sakurai et al. (1990) *Nature* 348: 732–735). Based on the amino acid sequence of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain. The distribution of receptor subtypes is tissue specific (Martin et al. (1989) *BioChem. Biophys. Res. Commun.* 162: 130–137). $ET_A$ receptors appear to be selective for endothelin-1 and are predominant in cardiovascular tissues. $ET_B$ receptors are predominant in noncardiovascular tissues, including the central nervous system and kidney, and interact with the three endothelin isopeptides (Sakurai et al. (1990) *Nature* 348: 732–734). In addition, the $ET_A$ receptors, which are endothelin-1-specific, occur on smooth muscle and are linked to vasoconstriction; whereas $ET_B$ receptors are located on the vascular endothelium and are linked to vasodilation (Takayanagi et al. (1991) *FEBS Lttrs.* 282: 103–106).

The activity of the endothelin isopeptides varies in different tissues by virtue of the distribution of receptor types and the differential affinity of each isopeptide for each receptor type. For example, endothelin-1 inhibits $^{125}$endothelin-1 binding in cardiovascular tissues 40–700 more potently than endothelin-3. $^{125}$Endothelin-1 binding in noncardiovascular tissues, such as kidney, adrenal gland, and cerebellum, is inhibited to the same extent by endothelin-1 and endothelin-3, which indicates that cardiovascular tissues are rich in $ET_A$ receptors and non-cardiovascular tissues are rich in $ET_B$ receptors.

Endothelin Structure/Function Relationships

Because it appears that endothelin has an important physiological function, studies of structural analogs of endothelin have been conducted in order to gain insight into its role in the patho-physiology of cardiovascular disorders, such as hypertension, atherosclerosis, cerebral and coronary vasospasm, asthma and renal failure. Such studies have demonstrated the importance of the two S—S bonds, the C-terminal Trp and the cluster of charged residues $Asp^8$-$Lys^9$-$Glu^{10}$ (see, Nishikori et al. (1991) *Neurochem. Int.* 18: 535–539) for vasoconstriction activity.

For example, studies using structural analogs have shown that the outer disulfide bond ($Cys^1$-$Cys^{15}$) bond is important for vasoconstrictor activity. A structural analog of endothelin-1 in which the outer disulfide bond ($Cys^1$-$Cys^{15}$) has been replaced with an amide linkage to produce ($Dpr^1$ (diamino-propionic acid)-$Asp^{15}$) endothelin-1 (Spinella et al. (1991) *Proc. Natl. Acad. Sci. USA* 88: 7443–7446) exhibited no agonist activity at $1\times10^{-7}$M but inhibited endothelin-1 induced pulmonary vasoconstriction at concentrations of $1\times10^{-7}$M and lower. It did not inhibit pulmonary vasoconstriction induced by thrombin, norepinephrine or endothelin-2, and competed effectively with labeled endothelin-1 for binding to cultured rat pulmonary artery smooth muscle cells. An analog which has the same sequence, but does not have the amide linkage, shows weak agonist activity and no antagonist activity.

The importance of each amino acid side chain functionality for receptor contact has been investigated. Alanine scans of endothelin in which each non-cysteinyl residue is individually substituted with an Ala (see, Castiglinone et al. (1991) in *Peptides: Chemistry and Biology, Proc. Amer. Pept. Symp.* (Twelfth)[J. A. Smith and J. E. Rivier, Eds.], ESCOM, Leiden, pp 402–403) or D-Ala (Galantino et al. (1991) in *Peptides: Chemistry and Biology, Proc. Amer. Pept. Symp.* (Twelfth)[J. A. Smith and J. E. Rivier, Eds.], ESCOM, Leiden, pp 404–405)) indicate that certain substitutions, such as replacement or deletion of the Trp residue, result in inactive peptides and other substitutions, such as replacement of the His enhance endothelin receptor binding and vasoconstriction activity compared to endothelin-1. Other studies have demonstrated that removal of the C-terminal tryptophan residue drastically diminishes the potency of endothelin-1 in inducing contraction of porcine coronary artery strips and in increasing the extracellular level of $Ca^{+2}$, which is required for vasoconstriction (Kimura et al. (1989) *Biochem. Biophys. Res. Commun.* 156: 1182–1186; Hirata et al. (1989) *Biochem. Biophys. Res. Commun.* 160: 228–234). Oxidation of the $Met^7$ does not alter activity. Amidation of the terminal COOH group decreases activity about 16-fold. Lys-Arg extension of the N-terminus reduces activity by 540-fold (Nakajima et al. (1989) *J. of Cardiovascular Pharm.* 13Suppl. 5): S1–S12).

Analogs in which the $Cys^1$ and $Cys^{15}$ have been replaced with Ala exhibit a 250-fold decrease in potency as a vasoconstrictor compared to endothelin-1, which has a $Cys^3$-$Cys^{11}$ and $Cys^1$-$Cys^{15}$ linkage. Switching the disulfide bonds to produce $Cys^1$-$Cys^{11}$ and $Cys^3$-$Cys^{15}$ or $Cys^1$-$Cys^3$ and $Cys^{11}$-$Cys^{15}$ also decreases the activity of the analog compared to endothelin-1. Replacement of the $Cys^3$ and $Cys^{11}$ with Ala only decreases potency by three-fold (Nakajima et al. (1989) *Biochem. Biophys. Res. Commun.* 163: 424–429). Opening the disulfide bond of endothelin, however, almost completely destroys the activity of endothelin-1 (Nakajima et al. (1989) *J. of Cardiovascular Pharm.* 13Suppl. 5): S1–S12).

The activities of C-terminal elongated derivatives (see, Nishikori et al., (1991) *Neurochem. Int.* 18: 535–539) have been studied. Except for the endothelin-22 elongated derivative, the binding affinities of the elongated derivatives for the $ET_A$ receptor are reduced compared to endothelin-1 and dependent upon amino acid number. Vasoconstrictor activities of some of the elongated derivative paralleled the binding affinities. Certain elongated derivatives, however, exhibit about the same activity as endothelin-38, the inactive endothelin-1 precursor.

Endothelin Antagonists

Among the compounds designed for study of the structure and function of endothelin, those that exhibit antagonistic activity to endothelin have been identified. In addition, a fermentation product of *Streptomyces misakiensis*, designated BE-18257B, has been identified as an $ET_A$ receptor antagonist (see, EP A1 0 436 189 to BANYU PHARMACEUTICAL CO., LTD (Oct. 7, 1991)). BE-18257B is a cyclic pentapeptide, c(D-Glu-L-Ala-allo-D-Ile-L-Leu-D-Trp), which inhibits $^{125}$endothelin-1 binding to cardiovascular receptors in a concentration-dependent manner, (IC$_{50}$ 1.4 µM in aortic smooth muscle membrane, 0.8 µM in ventricle membranes and 0.5 µM in cultured aortic smooth muscle cells), but fails to inhibit binding in endothelin$_B$ receptor-rich tissues at concentrations up to 100 µM has been identified. Cyclic pentapeptides related to BE-18257B, such as BQ-123 (c(D-Asp-Pro-D-Val-Leu-D-Trp)), have been synthesized and demonstrated to exhibit activity as endothelin-1 antagonists (see, EP A 10 436 189 to BANYU PHARMACEUTICAL CO., LTD (Oct. 7, 1991), see, also EP A2 0 460 679 to BANYU PHARMACEUTICAL CO., LTD (Dec. 11, 1991)). Studies of the ability of these cyclic peptides to inhibit receptor binding of endothelin-1 indicate that these cyclic peptides bind preferentially to ET$_A$ receptors.

The endothelin-1 analog [Ala$^{1,3,11,15}$]endothelin-1, in which the four cys residues are replaced with Ala, inhibits $^{125}$ET-1 binding to cerebral tissue, which is rich in ET$_B$ receptors (Hiley et al. (1989) *Trends Pharmacol. Sci* 10: 47–49). This peptide and certain truncated forms of endothelin-1 elicit dose-dependent relaxation of pre-contracted porcine pulmonary arteries to an extent that parallels the respective binding affinities of each form for the ET$_B$ receptor (Saeki et al. (1991) *Biochem. and Biophys Res. Commun.* 179: 286–292).

Because endothelin has a complex and diverse physiological role, compounds that act as specific antagonists or agonists may be therapeutically useful. In addition, compounds, which can specifically interfere with binding of endothelin peptides to ET$_A$ or ET$_B$ receptors should be useful in identifying essential characteristics of such agents and as disease specific therapeutic agents. The endothelin activity-modulating compounds that have been identified are peptides. Peptides tend to undergo extensive enzymatic degradation in vivo resulting in loss of bioactivity. Thus, such compounds may not be therapeutically effective and, certainly, are not ideally suited for pharmaceutical use. There is, therefore, a need for the identification of compounds that can act to modulate endothelin activity, particularly compounds that act as endothelin antagonists and agonists, but that are smaller than peptides and/or that are non-peptidic in nature and that are thereby more suitable for pharmaceutical use.

Therefore, it is an object herein to provide non-peptide compounds or compounds that are not solely composed of amino acids and peptide linkages and that modulate the activity of one or more of the endothelin isopeptides. It is another object herein, to provide compounds that are have activity as specific endothelin antagonists. It is also an object herein to provide compounds that are useful for treatment of disorders that are mediated by the action of endothelin. It is also an object herein to provide compounds that specifically interact with or inhibit the interaction of endothelin peptides with ET$_A$, ET$_B$ receptors or other ET receptors. It is also an object herein to provide methods for distinguishing between ET$_A$ and ET$_a$ receptors, for identifying endothelin-specific receptors, and for purifying such endothelin-specific receptors.

SUMMARY OF THE INVENTION

Compounds of formula (I):

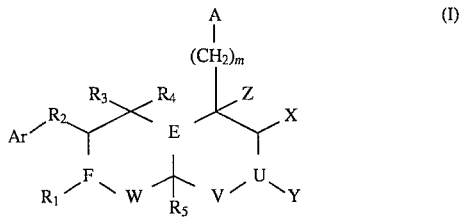

in which:

Ar is a substituted or unsubstituted aromatic or heteroaromatic group, including, but not limited to:

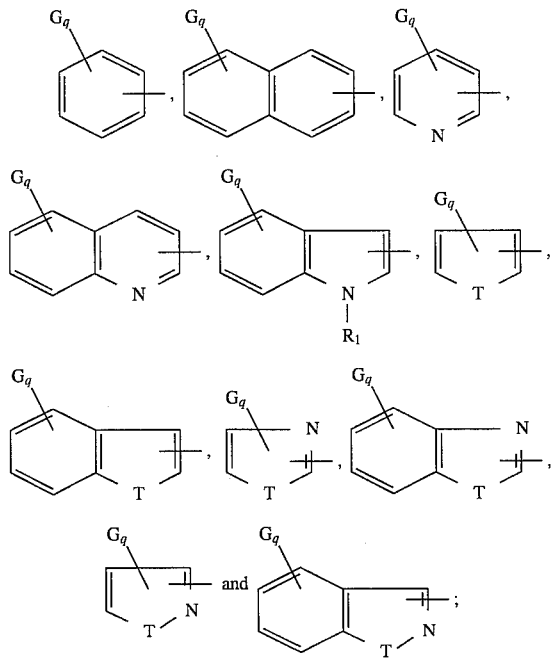

R is H or is a substituted or unsubstituted straight chain, branched chain, cyclic or acyclic alkyl, alkenyl, or alkynyl group having from 1–20 carbon atoms, preferably 1–10 carbon atoms, more preferably 1–8 carbon atoms and most preferably is a lower alkyl, alkenyl or alkynyl group having from 1–6 carbon atoms;

A is a functional group that bears a polar moiety and includes, but is not limited to: COOH, SO$_3$H, PO$_3$H, OH, CONHR, CON(R)$_2$, CONHSO$_2$R$_1$, SO$_2$NHCOR$_1$, CONHCOR$_1$ or tetrazole, which has the formula:

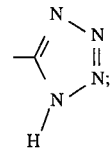

R$_1$, which is selected independently from R, is R, R—C=O, R substituted with one or more heteroatoms, including, but not limited to O, N, S, P, halogen, CN, N$_3$ or NO$_2$, or a substituted or unsubstituted aryl group, or is aryl-(CH$_2$)$_n$, in which the aryl group is preferably a lower aryl group and most preferably is Ar;

R$_2$ is (CH$_2$)$_n$, CHR, C(R)$_2$, COO, OCO, OCH$_2$, NHCO, CONH, SO, SO$_2$ or NR;

$R_3$ and $R_4$, which are the same or different or, independent of the other, each may be absent, and are =O, H, O-aryl, OR, O-alkyl or alkyl, aryl, SR, S-aryl, NHR, NH-aryl, NR, or other heteroaromatic groups, in which the alkyl and aryl groups are preferably lower alkyl or lower aryl and the aryl groups are preferably Ar;

$R_5$ is H, OH or R;

E and F, which are the same or are different, are N, $(CH_2)_p$, NR, or but preferably N or $(CH_2)_p$, and more preferably N or $(CH_2)_p$ such that at least one of E and F is N;

$G_q$, which is selected independent from $R_1$ and $R_3$, is $R_1$, $R_3$ halogen, CN, $NO_2$ or $N_3$;

p is an integer or 0 between 0 and 5, inclusive, and is preferably between 0 and 3, inclusive;

q is an integer or zero between 0 and 5, inclusive;

m and n are integers or 0 between 0 and 10, inclusive, and are preferably between 0 and 4, inclusive;

n, m, p and q, may be the same or different;

T is O, S, NR, or NCOR;

U and V, which may be the same or different, are $(CH_2)_n$;

W is CO, $C(R)_2$, $(CH_2)_n$, $(CH_2)_n$—CHR or CHR—$(CH_2)_n$;

X and Y. which may be the same or different, are H, alkyl or aryl or X and Y form a saturated or unsaturated, substituted or unsubstituted, homocyclic or heterocyclic ring contain 3–15 members, preferably 5–9 members; and Z is H, OH, OR, SR, NHR or $N(R)_2$ are provided.

In particular compounds of formula (I) that have formula (II) are preferred:

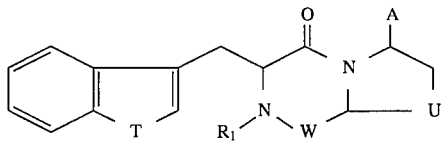

in which:

A is $CO_2H$, OH, O-alkyl or $NH_2$, in which the alkyl group is preferably an alkyl group having 1–10 carbon atoms and most preferably a lower alkyl group;

W is $CH_2$, $CH_2CHOH$, or CO;

n is an integer or 0 between 0 and 4, inclusive; and m is 0,

Other preferred compounds include those of formula II in which:

$R_1$ is as defined above, but is preferably an alkyl group, more preferably an alkyl group having 1–10 carbon atoms and most preferably a lower alkyl group;

E and F are N; and

T is NH, NCOR, $NCH_3$ or $NCH_2CH_3$.

Compositions containing therapeutically effective concentrations of the compounds of formula I formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, endotoxin shock, anaphylactic shock, hemorrhagic shock, and other diseases in which endothelin mediated physiological responses are implicated are provided.

Methods of treatment of hypertension, cardiovascular diseases, cardiac diseases including myocardial infarction, respiratory diseases, including asthma, inflammatory diseases, ophthalmologic diseases, gastroenteric diseases, renal failure, endotoxin shock, anaphylactic shock, hemorrhagic shock, and other diseases in which endothelin mediated physiological responses are implicated. using effective amounts of the compositions are also provided.

Methods for detecting, distinguishing and isolating endothelin receptors using the compounds of formula (I) are also provided.

BRIEF DESCRIPTION OF THE FIGURE

FIG. 1 sets forth preferred synthesis schemes for synthesis of the compounds of formula (I). The numbers in parenthesis refer to the products of the particular schemes described below.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference herein.

As used herein, a peptidomimetic is a compound that mimics the conformation and certain stereochemical features of the biologically active form of a particular peptide. In general, peptidomimetics are designed to mimic certain desirable properties of a compound but not the undesirable features, such as flexibility leading to a loss of the biologically active conformation and bond breakdown. For example, methylenethio bioisostere [$CH_2S$] has been used as an amide replacement in enkephalin analogs (see, e.g., Spatola, A. F. *Chemistry and Biochemistry of Amino Acids, Peptides, and Proteins* (Weistein, B, Ed.), Vol. 7, pp. 267–357, Marcel Dekker, New York (1983); and Szelke et al., *In Peptides: Structure and Function, Proceedings of the Eighth American Peptide Symposium*, (Hruby and Rich, Eds.); pp. 579–582, Pierce Chemical Co., Rockford, Ill. (1983)).

A peptidomimetic is, thus, a compound that mimics certain properties of a peptide. For example, morphine is a compound which can be orally administered, and which is a peptidomimetic of the peptide endorphin.

As used herein, endothelin peptides include peptides that have substantially the amino acid sequence of endothelin-1, endothelin-2, endothelin-3 and that act as potent endogenous vasoconstrictor peptides.

As used herein, endothelin antagonists include compounds that inhibit endothelin-stimulated vasoconstriction and contractions and other endothelin-mediated physiological responses. The antagonist may act by interfering with interaction of the endothelin with an endothelin-specific receptor or by interfering with the physiological response or bioactivity of endothelin, such as vasoconstriction. The effectiveness of a potential antagonist can be assessed using methods known to those of skill in the art. For example, the properties of potential antagonist may be assessed as a function of its ability to inhibit an endothelin induced activity in vitro using a particular tissue, such as rat portal vein and aorta as well as rat uterus, trachea and vas deferens (see e.g., Borges, R., Von Grafenstein, H. and Knight, D. E. (1989) Tissue selectivity of endothelin, *Eur. J. Pharmacol* 165: 223–230). The ability to act as an endothelin antagonist in vivo can be tested in hypertensive rats, ddy mice or other recognized animal model (see, Kaltenbronn et al. (1990) *J. Med. Chem.* 33: 838–845, see, also EP A 10 436 189 to BANYU PHARMACEUTICAL CO., LTD (Oct. 7, 1991); see, also Bolger et al. (1983) *J. Pharmacol. Exp. Ther.* 225291–309).

As used herein, an endothelin antagonist interferes with endothelin-stimulated vasoconstriction or that competitively inhibit binding of endothelin to particular receptors, such as $ET_A$ receptors, as assessed by assays known to those of skill in the art. For example, endothelin activity can be identified by the ability of endothelin to stimulate vasoconstriction of isolated rat thoracic aorta or portal vein ring segments (Borges et al. (1989) "Tissue selectivity of endothelin" *Eur. J. Pharmacol.* 165: 223–230). To perform the assay, the endothelium is abraded and ring segments are mounted under tension on stirrups in a tissue bath and exposed to endothelin in the presence of the test compound or compounds. Changes in endothelin-induced tension are recorded. Dose response curves may be generated and used to provide information regarding the relative potency of the test compound. Other tissues that may be used for evaluating the effects on tissue contraction include heart, skeletal muscle, kidney, uterus, trachea and vas deferens. Endothelin receptor isotype specific antagonist compounds may be identified by the ability of such compounds to interfere with endothelin binding to different tissues or cells expressing specific endothelin-receptor subtypes, or to interfere with biological effects of endothelin or an endothelin isotype, thereby exhibiting endothelin-receptor subtype specificity. For example, $ET_B$ receptors are expressed in vascular endothelial cells, possibly mediating the release of prostacyclin and endothelium-derived relaxing factor (De Nucci et al. (1988) *Proc. Natl. Acad. Sci. USA* 85:9797). $ET_A$ receptors are not detected in cultured endothelial cells, which express $ET_B$ receptors. For example, the binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, e.g., Filep et al. (1991) *Biochem. and Biophys Res. Commun.* 177: 171–176).

Thus, the relative affinity of the compounds for different endothelin receptors may be evaluated by determining dose response curves to using tissues that differ in receptor subtype.

As used herein, the biological activity or bioactivity of endothelin includes any activity induced, potentiated or influenced by endothelin in vivo. It also includes the ability to bind to particular receptors and to induce a functional response, such as vasoconstriction. These activities, which appear to be a function of the receptor subtype expressed in a particular tissue, include, but are not limited to, vasoconstriction, vasorelaxation and bronchodilation. For example, $ET_B$ receptors appear to be expressed in vascular endothelial cells and may mediate vasodilation and other such responses; whereas $ET_A$ receptors, which are endothelin-1-specific, occur on smooth muscle and are linked to vasoconstriction Any assay known to those of skill in the art to measure or detect such activity may be used to assess such activity (see, e.g., Spokes et al. (19989) *J. Cardiovasc. Pharmacol.* 13(*Suppl.* 5):S191–S192; Spinella et al. (1991) *Proc. Natl. Acad. Sci. USA* 88: 7443–7446; Cardell et al. (1991) *Neurochem. Int.* 18: 571–574; and the Examples herein).

As used herein, the $IC_{50}$ refers to 50% of inhibition of the maximal response, such as binding of endothelin to tissue receptors.

As used herein, $EC_{50}$ refers to 50% of maximal expression of a particular response induced, provoked or potentiated by a particular test compound.

As used herein, a lower alkyl or lower alkenyl refers to a carbon chain that contains six or fewer carbons. Such chains may be branched, straight, cyclic or any combination of branched, straight and cyclic.

As used herein, a non-peptidic compound refers to compounds that do not include more than two linked amino acids and that include linkages other than peptide bonds among the constituent groups.

As used herein, biological activity refers the in vivo activities of a compound or physiological responses that result upon in vivo administration of a compound, composition or other mixture. Biological activity, thus, encompasses therapeutical effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound.

As used herein, definitions of substituents are limited to forms that could, by virtue of the principles of chemistry, exist. Thus, unless otherwise specified, it is implicit that carbon has four bonds, whether single, double or conjugated, in any of the compounds encompassed by the formulas set forth herein.

As used herein, the abbreviations for amino acids and protective group are in accord with their common usage and the IUPAC-IUB Commission on Biochemical Nomenclature (see,(1972) *Biochem.* 11: 1726). Each amino acid is identified by the standard three letter code for the naturally occurring L-amino acids; the prefix "D" indicates that the stereoisomeric form of the amino acid is D.

Description of the Compounds that Modulate Endothelin Activity

Compounds that contain two or more fused substituted or unsubstituted, saturated or unsaturated heterocyclic rings that modulate the in vivo or in vitro activity of at least one endothelin isopeptide are provided. More particularly, compounds of formula I, defined above, and pharmaceutically acceptable salts, esters and prodrugs thereof are provided.

Preferred compounds include those of formula I that have formula II, defined above. More preferred compounds of formula (I) are those with formulas III–XI:

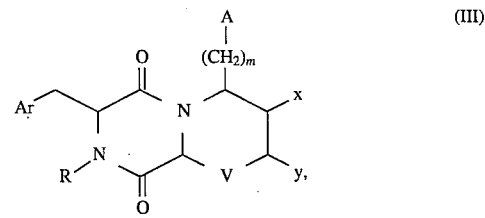

(III)

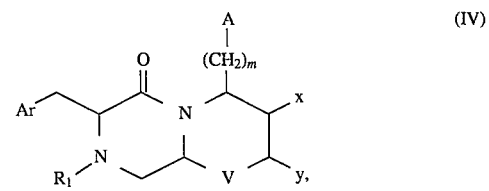

(IV)

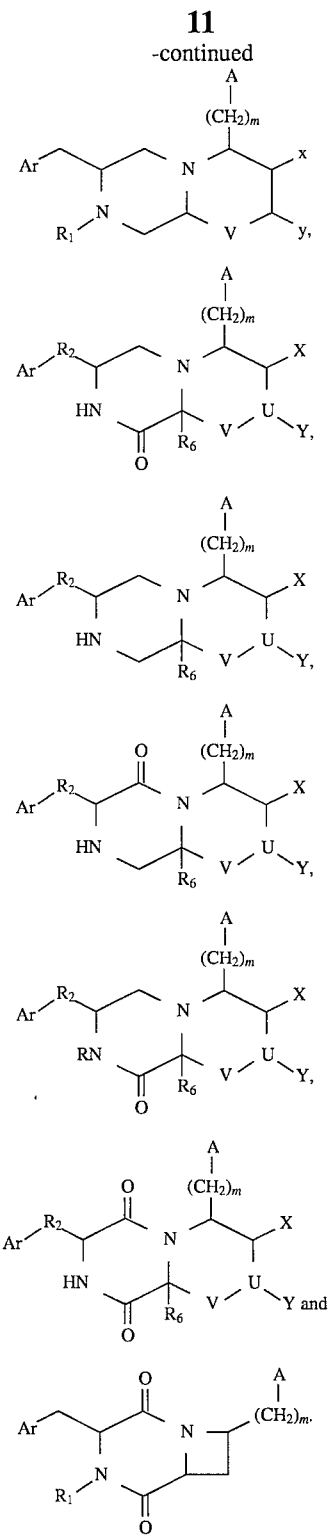

A more preferred compound is 3-(3-indolylmethyl)-1,4-diaza-2,5-dioxo-bicyclo[4.3,0]nonane-9-carboxylic acid of formula XII:

Most preferred compounds include pharmaceutically active stereoisomers of formula XII, particularly the (3S, 6R, 9S) stereoisomer of the compound of formula III with the structure represented by formula XIII:

Methods for Synthesis of the Compounds that Modulate Endothelin Activity

The compounds of formula (I) may be prepared by any suitable synthetic scheme, Such schemes should be apparent to one of skill in this art. For example, the compounds may be synthesized by hydrogenation of the corresponding aromatic or heteroaromatic compounds which can be synthesized by standard methods (see, e.g., *Hydrogenation Methods* Rylander, Academic Press, New York, 1990 and *Comprehensive heterocyclic Chemistry* Katritzky et al. eds., Pergamon Press, Oxford, 1980). In particular, the piperazines can be synthesized from the corresponding protected α-amino acids and N-(2-carboalkoxy)-alkyl-α-amino acids according to the following processes, which are represented schematically in FIG. 1.

(1) Synthesis of the compounds in which E and F are N, W is=O and $R_3$ or $R_4$ is=O The piperazine-2,5-diones can be prepared by coupling an N-protected α-amino acid with an N-(2-carboalkoxy)alkyl α-amino acid ester under standard, well known, peptide coupling conditions to form the corresponding dipeptide which is then deprotected and cyclized to the produce the compounds described herein.

(2) Synthesis of the compounds in which E and F are N, W is $CH_2$, CHR or RCR, $R_3$ is absent and $R_4$ is=O To produce the compounds of formula (I) in which E and F are N, W is $CH_2$, CHR or RCR, $R_3$ is absent and $R_4$ is=O, the intermediate amide ester can be reduced to the amide alcohol using suitable reducing agents, including, but not limited to, sodium borohydride and dilosbutylaluminum hydride, and then cyclized to give 2-piperazinones.

(3) Synthesis of the compounds in which E and F are N, W is=O, $R_3$ and $R_4$ are, independently, H or R To produce the compounds of formula (I) in which E and F are N, W is=O, $R_3$ and $R_4$ are H or R, the intermediate amides can be reduced to the amine with reducing agents, such as, but not limited to, diborane. Subsequent cyclization as described in (1) can produce 5-piperazinones.

(4) Synthesis of the piperazine compounds in which E and F are N and W is $CH_2$ The piperazines can be produced by reduction of the piperazine-2,5-diones ((1), above) with diborane, aluminum hydride or lithium aluminum hydride. Introduction of $R_1$ at N-4 in these compounds may be effected by alkylation or acylation reactions known to those skilled in the art of organic synthesis to produce the corresponding 4-substituted compounds.

A preferred scheme for synthesis of the compounds provided herein is presented in FIG. 1.

Pharmaceutically acceptable salts, esters of the compounds provided herein may be prepared by any suitable method known to those of skill in this art. Stereoisomers may be separated by methods, such as recrystallization and high performance liquid chromatography (HPLC) separation, known to those of skill in this art (for a review of numerous procedures, see, e.g., Jacques et al. (1981) *Enantiomers, Racemates, and Resolutions,* John Wiley & Sons, New York).

Description of Compositions Containing the Compounds

Pharmaceutical compositions containing therapeutically effective concentrations of at least one of the compounds of formula I, salts or esters thereof, in a pharmaceutically acceptable carrier are provided.

The concentrations of compounds provided herein include those that are therapeutically effective for treatment of hypertension, cardiovascular diseases, cardiac diseases including myocardial infarction, respiratory diseases, including asthma, inflammatory diseases, ophthalmologic diseases, gastroenteric diseases, renal failure, endotoxin shock, anaphylactic shock, hemorrhagic shock, and other diseases in which endothelin mediated physiological responses are implicated.

Evaluation of the Bioactivity of the Compounds

After synthesis, the bioactivity of the compounds may be evaluated. Standard physiological, pharmacological and biochemical procedures are available for testing the compounds to ascertain whether the compound possess any biological activities of an endothelin peptide or the ability to interfere with, inhibit or potentiate the activity of endothelin peptides.

Screening Compounds for the Ability to Modulate the Activity of an Endothelin Peptide Numerous assays are known to those of skill in the art for evaluating the ability of compounds to modulate the activity of endothelin (see, e.g., EP A1 0 436 189 to BANYU PHARMACEUTICAL CO., LTD (Oct. 7, 1991); Borges et al. (1989) *Eur. J. Pharm.* 165: 223–230; Filep et al. (1991) *Biochem. Biophys. Res. Commun.* 177: 171–176). For example, assays that assess the induction or inhibition of the contractile response of thoracic aorta tissue to endothelin-1 or endothelin-1 analogs, antagonists and agonists may be used to detect compounds that exhibit antagonist or agonist activity (see, Borges et al. (1989) *Eur. J. Pharmacol.* 165: 223–230). The binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, e.g., Ogawa et al. (1991) *Biochem. and Biopys Res. Commun.* 178: 248–255).

In vitro studies may be corroborated with in vivo animal studies (see, e.g., EP A1 0 436 189 to BANYU PHARMACEUTICAL CO., LTD. (Oct. 7, 1991)) from which effective dosages for treatment of animals, including humans, may be extrapolated (see, e.g., Bolger et al. (1983) *J. Pharmacol. Exp. Ther..* 225291–309).

Using such assays, the relative affinities of the compounds for $ET_A$ receptors and $ET_B$ receptors may be assessed and those that possess the desired properties, such as specific inhibition of binding of endothelin-1, may be selected. The selected compounds that exhibit activities that may be therapeutically useful may be formulated in suitable pharmaceutical compositions.

Formulation of Pharmaceutical Compositions

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients.

The active compounds can be administered by any appropriate route, for example, orally, parenterally, intravenously, intradermally, subcutaneously, or topically, in liquid, semi-liquid or solid form and are formulated in a manner suitable for each route of administration.

The active compound is included in the pharmaceutically acceptable carrier in an amount sufficient to exert a therapeutically useful effect in the absence of serious toxic effects on the patient treated. The therapeutically effective concentration may be determined empirically by testing the compounds in known in vitro and in vivo systems (see, e.g., EP A1 0 436 189 to BANYU PHARMACEUTICAL CO., LTD (Oct. 7, 1991); Borges et al. (1989) *Eur. J. Pharm.* 165: 223–230; Filep et al. (1991) *Biochem. Biophys. Res. Commun.* 177: 171–176).

The concentration of active compound in the drug composition will depend on absorption, inactivation, excretion rates of the active compound, the dosage schedule, and amount administered as well as other factors known to those of skill in the art.

Typically a therapeutically effective dosage should produce a serum concentration of active ingredient of from about 0.1 ng/ml to about 50–100 μg/ml/kg body weight. The pharmaceutical compositions typically should provide a dosage of from about 0.01 to about 50 mg of compound per kilogram of body weight per day. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired therapeutic effect or with materials that supplement the desired action, such as, for example, if the compound is used for treating asthma or hypertension, with other bronchodilators and antihypertensive agrents, respectively.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening agents, such as glucose, polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

The compounds may be formulated for local or topical application, such as for topical application to the skin in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The compounds may be formulated as aeorsols for topical application, such as by inhalation (see, e.g., U.S. Pat. Nos. 4,044,126, 4,414,209, and 4,364,923, which describe aerosols for delivery of asteroid useful for treatment inflammatory diseases, particularly asthma).

Affinity Isolation of Endothelin Receptors

The compounds may be used in methods for identifying and isolating endothelin-specific receptors. One or more of the compounds may be linked, covalently or by other linkage, to an appropriate resin or other support, such as Affi-gel, by methods known to those of skill in the art, such as methods in which like compounds are bound to such resins (see, e.g., Schvartz et al. (1990) *Endocrinology* 126:3218–3222). The selected compound or compounds may be one or those that is (are) specific for $E_A$ or $E_B$ receptors or other subclass of receptor. The resin is pre-equilibrated with a suitable buffer at a physiological pH (pH 7–8). A composition containing solubilized receptors from a selected tissue are contacted with the resin to which the compound is bound and the receptors are selectively eluted and identified by testing them for binding to an endothelin peptide. Preparation of the receptors and resin and elution may be performed by modification of standard protocols known to those of skill in the art (see, e.g., Schvartz et al. (1990) *Endocrinology* 126: 3218–3222).

The following examples are included for illustrative purposes only and are not intended to limit the scope of the invention.

EXAMPLE 1

Preparation of (±) trans-2,5-Dicarbethoxypyrrolidine (1)

1.7 g (27 mmol) of ammonium formate and 0.17 g of 10% Pd/C was added to a solution of 1.02 g (3.34 mmol) of (±)-trans-2,5 -dicarbethoxy-N-benzylpyrrolidine in 5.0 ml of dry ethanol. The resulting black suspension was stirred under an atmosphere of argon at reflux temperature for a period of 8 hr during which gases evolved. Thin layer chromatographic (TLC) analysis of the mixture (1:3; EtOAc/hexane) confirmed the disappearance of the starting material and the appearance of a new spot at the origin.

Stirring was then discontinued, the reaction mixture was filtered though a pad of Celite and washed with ethanol. The ethanol was removed in vacuo and the remaining suspension was dissolved in 40 ml of ethyl acetate, washed with water (2×5 ml) and brine (1×5 ml), and dried over anhydrous $MgSO_4$. Concentration in vacuo produced 0.72 g (76.6%) of a clear colorless oil that was homogenous as evidenced TLC (R,0.42, 1:2 EtOAc/Hexane) and that had the following 1H NMR data: (CDCl₃,360 MHZ) spectroscopic data:

δ 4.09–4.29 (4H,m) 3.94–4.06 (2H,m), 2.83–3.03 (1H,br s), 2.59–2.68 (2H,m), 1.89–2.39 (2H,m), 1.21–1.43 (6H,t).

Preparation of boc-D-Trp-(±) trans-2,5-dicarbethoxypyrrolidine (2)

3.9 g (19 mmol) of 1,3-dicyclohexylcarbodiimide (DCC) was added at 0° C. to a solution containing 1.63 g (7.58 mmol) of (±)-trans -2,5dicarbethoxypyrrolidine (1), 2.54 g (11 mmol) of Boc-D-tryptophan, 2.56 g (19 mmol) of 1-hydroxy benzotriazole hydrate, 3.3 ml (19 mmol) of diisopropyloethylamine in 25 ml of dry dimethylformamide (DMF). The resulting clear colorless solution was stirred under an argon atmosphere at room temperature for a period of 18 hr which resulted in the formation of a white precipitate. TLC analysis of the mixture (97:3 CHCl₃/MeOH) indicated that there was some remaining pyrrolidine diester. Therefore, an 2.0 g of DCC was added and the solution was stirred for an additional 5 hr at room temperature. Ethyl acetate (80 ml) was added to the reaction mixture and the solution was washed with water (3×25 ml) and brine solution (1×25 ml), and dried over MgSO₄. Solvents were removed in vacuo and to produce 4.53 g of a thick yellow oil. Chromatography of the crude product on silica gel using the eluent showed that the product was a diastereomeric mixture (Rf=0.29 and 0.25) of the coupled products in an approximate ratio of 1.5:1. Total yield for both of the fractions containing the tryptophan pyrrolidine diester was 1.69 g (44.6%). The diastereomer possessing the higher R_f(0.29) was separated and analyzed yielding the following 1H NMR (CDCl₃, 360 MHz) spectroscopic data:

8.04–8.11 (1H,br s), 7.73–7.79 (1H,d), 7.32–7.38 (1H,d), 7.10–7.24 (3H,m), 5.27–5.34 (1H,d), 4.54–4.68 (2H,m), 4.05–4.28 (4H,m), 3.90–3.97 (1h,d), 3.13–3.22 (2H,d), 1.36–1,42 (4H,m), 1.18–1.42 (m,15H)

Preparation of D-tryptophanyl-trans-2,5-dicarbethoxypyrrolidine (3)

A 25% solution of TFA in CH₂Cl₂ (25 ml) was added at 0° C. to an isomeric mixture 0.94 g (1.9 mmol) of the tryptophan pyrrolidine diester (2) and 0.41 g (3.8 mmol) anisole. The reaction mixture was stirred at 0° C. for 15 min and then at room temperature for 2. hr. TLC analysis (93:7, CHCl₃/MeOH) using a ninhydrin indicator showed the complete disappearance of the starting material and the appearance of a new spot near the baseline. Without isolation of this material, the TFA was neutralized by the addition of 12.12 ml of diisopropylethylamine and the mixture turned from dark red to yellow. After stirring at room temperature for approximately six hours, TLC analysis of the reaction mixture (95:5;CHCl₃/MeOH) showed the presence of two major isomers in approximately a 2:1 ratio. After removal of the CH₂Cl₂ in vacuo, the suspension was extracted into ethyl acetate and washed and dried over anhydrous MgSO₄. Concentration in vacuo resulted in 0.88 g of a dark brown oil. Column chromatography over silica gel (CHCl₃) produced 0.30g (44%) of the trans isomer that yielded the following ¹H NMR (CDCl₃, 360 MHz) data:

δ 0.18–8.34 (1H,br s), 7.48–7.62 (1H,d), 7.29–7.43 (1H, d), 7.00–7.28 (3H,m), 5.66–5.83 (1H,s), 4.51–4.63 (1H,t), 4.38–4.50 (1H,m), 4.12–4.43 (3H,m), 3.62–3.78 (1H,m), 2.86–3.02 (1H,m), 2.23–2.43 (2H,m), 1.83–2.12 (2H,m), 1.24–1.36 (3H,t).

Further elution with chloroform gave 0.15 g of the cis isomer (m.p. 144°–149° C.) that had the following ¹H NMR (CDCl₃, 360 MHz) spectroscopic data:

8.19–8.39 (1H,br s), 7.49–7.61 (1H,d), 7.29–7.43 (1H,d), 7.01–7.28 (3H,m), 6.21 (1H,br s), 4.62 (1H,t), 4.23–4.34 (3H,m), 3.81–3.93 (1H,m), 1.73–1.05 (2H,m), 1.25–1.36 (3H,t).

Preparation of 3-(3-indolylmethyl)-1,4-diaza-2,5-dioxobicyclo [4.3.0]nonane-9-carboxylic acid (4)

A 1N NaOH solution 90 μl (0.09 mmol) was added to a solution of 0.032 g (0.09 mmol) of D-tryptophanyl-trans-2, 5-dicarbethoxypyrrolidine (3) dissolved in 3.0 ml of methanol-water solution. The clear solution was stirred at room temperature for approximately 3 hr. TLC analysis indicated that only a trace of unreacted starting material (95:5; CHCl₃/MeOh) was present. Ethyl acetate (2.0 ml) was added to the solution and the mixture was transferred to a separatory funnel in which, following dilution with about 4 ml of water, two layers separated. The aqueous layer was then acidified to about pH 2 with 0.05N HCl when brown oil droplets fell out of the aqueous layer and extracted with ethyl acetate (2×20 ml), and the extract was dried over MgSO₄. Concentration of the solvents in vacuo produced 18.6 mg (63.9%) of a crude product that appeared as a semi-white crystalline powder.

TLC of this material (85:10:5; CHCl₃/MeOH/AcOH) showed two major spots in an approximate ratio of 1:1.

EXAMPLE 2

A. Endothelin Binding Inhibition Binding Test #1

TE 671 cells (ATCC Accession No. HTB 139) were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. at 57,800×g for 15 min, the pellet was resuspended in 5 ml of buffer A (5 mM HEPES buffer, pH 7.4 containing aprotinin (100 KIU/ml)) and then frozen and thawed once. 5 ml of Buffer B (5 mM HEPES Buffer, pH 7.4 containing 10 mM MnCl₂ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml and stored at −70° C. until use.

The membrane suspension was diluted with binding buffer (30 mM HEPES buffer, pH 7.4 containing 150 mM NaCl, 5 mM MgCl₂, 0.5% Bacitracin, 0.1% BSA) to a concentration of 6 μg/100 μl. To this suspension 50 μl of (A) endothelin-1 (for non specific binding: to give a final concentration 80 nM), (B) binding buffer (for total binding), or (C) a test compound (final concentration 1 nM to 100 μM) were added. Mixtures were shaken and incubated at 25° C. for 60 minutes prior to the addition of 50 μl ¹²⁵I-ET-1 (3,000 cpm). Mixtures were shaken, incubated at 4° C. for 16 hours and centrifuged at 4° C. for 25 min at 2,500×g. The supernatant, containing unbound radioactivity, was decanted and the pellet counted on a Genesys multiwell gamma counter. The degree of inhibition of binding (D) was calculated according to the following equation:

$$\%D = 100 - \frac{(C)-(A)}{(B)-(A)} \times 100$$

Each test was performed in triplicate.

Endothelin Inhibition binding test #2

COS7 cells were transfected with DNA encoding the $ET_B$ receptor, The resulting cells, which express the human $ET_B$ receptor, were grown to confluence in T-150 flasks. Membrane was prepared as described above. The binding assay was performed as described above using the membrane preparation diluted with binding buffer to a concentration of 1 µg/100 µl.

Test Results

The test results are set forth in TABLE 1:

TABLE 1

| TEST COMPOUND | $IC_{50}$ µM |
|---|---|
| 3-(3-indolylmethyl)-1,4-diaza-2,5-dioxo-bicyclo[4.3.0]nonane-9-carboxylic acid | 22.5 |

Endothelin Binding Inhibition Binding Test #2

The COS7 cells, described above, that had been transfected with DNA encoding the $ET_B$ receptor and express the human $ET_B$ receptor were grown to confluence in T-175 flasks. Cells from multiple flasks were collected by scraping, pooled and centrifuged for 10 min. at 190×g. The cells were resuspended in phosphate buffered saline (PBS) containing 10 mM EDTA using a Tenbroeck homogenizer. The suspension was centrifuged at 4° C. at 57,800×g for 15 min, the pellet was resuspended in 5 ml of buffer A (5mM HEPES buffer, pH 7.4 containing aprotinin (100 KIU/ml)) and then frozen and thawed once. 5 ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml.

The binding assay was performed as described above using the membrane preparation diluted to give 1 µg/100 µl of binding buffer.

Test Results The test compound 3-(3-indolylmethyl)-1,4-diaza-2,5-dioxobicyclo[4.3.0]nonane-9-carboxylic acid showed no detectable activity in the second binding inhibition assay.

Effect on Endothelin Induced Contraction of the Isolated Rat Thoracic Arterial Ring The effectiveness of the test compound as an antagonist or agonist of the biological tissue response of endothelin can assessed by measuring the effect on endothelin induced contraction of isolated rat thoracic arterial ring (see, e.g., Borges et al. (1989) *Eur. J. Pharmacol.* 165: 223–230).

Since modifications will be apparent to those of skill in this art, it is intended that this invention be limited only by the scope of the appended claims.

We claim:

1. A compound that is 3-(3-indolylmethyl)-1,4-diaza-2,5-dioxo-bicyclo[4.3.0]nonane-9-carboxylic acid, which has the formula:

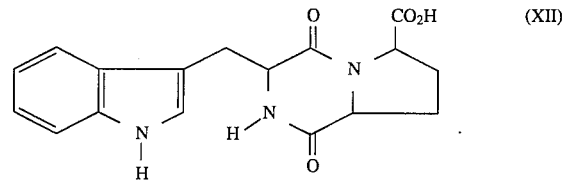

2. A compound selected from the group consisting of

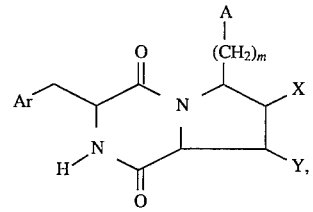

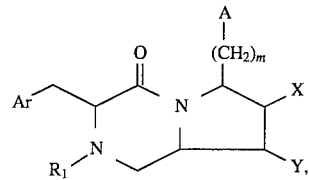

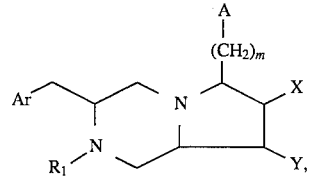

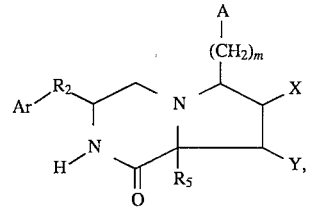

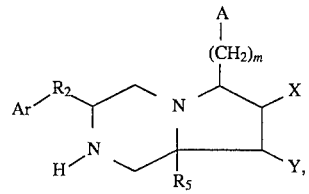

-continued

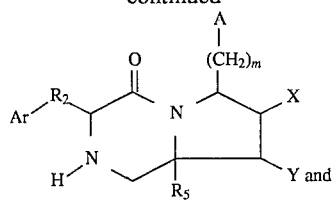

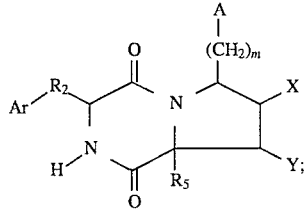

wherein:

Ar is

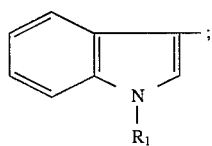

X and Y are H;

m is 0;

A is OH, COOH or COH;

$R_1$ is H or H—C=O;

$R_5$ is H or OH; and $R_2$ is $CH_2$.

3. A compound that has formula (II):

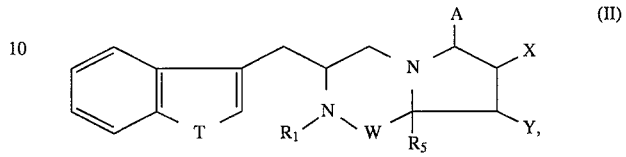

wherein:

A is OH COOH or COH;

$R_1$ is H or R;

R is a straight or branched chain lower alkyl group;

$R_5$ is H or OH;

X and Y are H;

T is NH, $NCH_3$ or $NCH_2CH_3$;

W is $CH_2$ or CO.

4. The compounds of claim 3, wherein $R_1$ is H.

5. The compounds of claim 4, wherein T is NH.

6. The compounds of claim 3, wherein $R_1$ is H.

* * * * *